US005703923A

United States Patent [19]
Bardash

[11] Patent Number: 5,703,923
[45] Date of Patent: Dec. 30, 1997

[54] THREE DIMENSIONAL IMAGING SYSTEM USING LASER GENERATED ULTRASHORT X-RAY PULSER

[75] Inventor: Michael J. Bardash, Brooklyn, N.Y.

[73] Assignee: QEL Inc., Brooklyn, N.Y.

[21] Appl. No.: 748,501

[22] Filed: Nov. 8, 1996

Related U.S. Application Data

[62] Division of Ser. No. 285,821, Aug. 4, 1994, Pat. No. 5,602,894.

[51] Int. Cl.⁶ .................................................. G01N 23/201
[52] U.S. Cl. .................................................. 378/87; 378/4
[58] Field of Search .............................. 378/87, 70, 76, 378/4, 86, 901, 62

[56] References Cited

U.S. PATENT DOCUMENTS

5,247,561  9/1993  Kotowski ................................ 378/87

Primary Examiner—Don Wong
Attorney, Agent, or Firm—Gottlieb, Rackman & Reisman, P.C.

[57] ABSTRACT

An apparatus for imaging the interior of an object illuminates the object with a source of picosecond collimated x-ray pulses. An array of x-ray detectors senses pulses of Compton scattered x-rays from the object and a processor accumulates the data to construct an image of the object by accumulating data from ellipsoidal sections of the object.

8 Claims, 12 Drawing Sheets

THREE DIMENSIONAL IMAGING SYSTEM USING LASER GENERATED ULTRASHORT X-RAY PULSER

This is a division of application Ser. No. 08/285,821, filed Aug. 4, 1994 now U.S. Pat. No. 5,602,894.

BACKGROUND OF THE INVENTION

1. Field of Invention

This invention relates to x-ray tomography. More generally it relates to an apparatus and method for acquiring three dimensional images showing the composition and shape of the interior of an object. More particularly, it provides three dimensional images derived from Compton scattered x-ray signals measured by several detectors that result when the object is irradiated with a substantially point source of ultrashort x-ray pulses. The invention also relates to the apparatus for producing and detecting such point source ultrashort x-ray pulses.

2. Prior Art

Currently most x-ray scanners use a tomographic technique for creating images. This involves measuring the amount of energy lost along many different lines of sight that all lie in a single slab. The slab is broken up into small volumes, or pixels, and based on the line of sight information, the amount of energy lost in each pixel is calculated. The cross section and density information for that pixel is then recovered. In practice, this results in a two dimensional image that has a certain thickness. Three dimensional information is recovered by moving the object that is being imaged.

Another three dimensional technique has been proposed based on the concept of photon migration. See, for example, U.S. Pat. 4,857,748 issued Aug. 15, 1989. This entails radiating a sample with ultrashort optical pulses and measuring the time evolution of the transmitted and reflected signals along a line of sight. Both of these signals include not only directly transmitted or reflected photons, but also photons which may be scattered several times inside the material and then reemerge. These photons are said to be diffusing or migrating through the object and might contain information regarding the structure of the object. This approach suffers from several problems. First and foremost, most materials are too optically "thick" to provide any information. Additionally, optical photons can have very complex paths before they reemerge and the mathematical unfolding of these signals to determine the structures that have scattered or reflected them is virtually an intractable problem.

Methods are also known for recognizing in photographic data curves having pre-determined configurations. For example U.S. Pat. No. 3,069,654 to Hough, issued Dec. 18, 1962, describes apparatus for determining the presence of straight lines in a photograph. The original use of this technique was to automate the determination of the presence of linear particle tracks in bubble chamber photographs.

The Hough invention recognizes the presence of markers in a photograph lying along a line in the photograph by first associating each unique marker in the photograph with a corresponding unique line in a second space. The association is done so that the lines in the second space form bundles passing through points (called knots) in the second space only if the associated markers lie on a straight line. Thus by looking for knots in the second space one locates all the lines on which the markers lie.

In particular if $(x,y)$ is the location of the marker, then according to the Hough patent the associated line in the second space is defined by the equation $y'=(x'-x)/y$. See column 1, line 70 to column 2, line 7). It's then a simple matter of algebra to show that a collection of markers satisfying the linear relationship $y=mx+b$ has associated lines that all intersect at the so-called "knot" $(x',y')=(-b/m, -1/m)$. Once the coordinates of the knot $(x',y')$ are determined by inspection of the lines in the second space, the line in the photograph along which the markers lie is determined by the equation $y=-x/y'+x'y'$.

The above association is known as a Hough transformation and has been generalized for curves other than straight lines. See for example Duda, R. O. and Hart, P. E. "Uses of the Hough Transformation to detect lines and curves in pictures", 15 Comm ACM, 1972, p.11; and Kimme et al., "Finding Circles by an Array of Accumulators", [18] Comm ACM, 1975, p. 120. Kimme describes the use of the generalized Hough technique to recognize circles in x-rays, something that is useful where tumors are spherical. These techniques differ from the present invention because they seek only details of pre-determined configuration.

BRIEF DESCRIPTION OF THE INVENTION

The present invention irradiates an object with an x-ray beam, and observes the photons scattered out of the beam into a large solid angle. The number of scattered photons that arise from any small volume, herein termed a "voxel", is determined by the Compton scattering cross section for the material in that volume. This cross section is a known function of the object's electron density and the x-ray beam's energy spectrum. Namely, the Klein-Nishina spectrum. The x-ray beam's spectrum is measured, and the density of material in any voxel in the object is determined by measuring the number of photons undergoing Compton scattering from that voxel.

This invention employs a method having the steps of irradiating an object with pulses from a point source that produces ultrashort x-ray pulses and reconstructing a three dimensional image from measurements of the time evolution of the Compton scattering from the object at several locations in space. The point source ultrashort x-ray pulses are produced from a high intensity optical laser pulse that is used to produce an electron beam that in turn produces the x-rays, for example by Bremsstrahlung emission.

The invention enables therapeutic x-rays (e.g. high energy x-rays used for cancer therapy) to be imaged resulting in a three dimensional depiction of the dose delivered to the patient.

It is an object of the present invention to provide an apparatus and method for measuring the three dimensional composition and structure of an object opaque to ordinary light in a non-invasive manner using ultrashort x-ray pulses of photons that each undergo a single Compton scattering event in passing through the object and by correlating the time of arrival of the scattered photon at a detector with its time of emission from its source.

It is another object of the present invention to provide an apparatus for delivering ultra-short x-radiation doses to an object or patient, monitoring the radiation re-emitted by that object and reconstructing a three dimensional image of the object which re-emitted the radiation.

It is yet another object of the present invention to provide a three dimensional image of therapeutic x-rays dosages received by a patient.

It is a further object of this invention to provide a processor that is capable of extracting image data from the measured re-emitted x-ray data produced by Compton scattering of ultra-short x-ray pulses by the object under investigation.

To attain these objects there are two preferred embodiments of the x-ray source of the invention. According to the first embodiment of the invention there is provided an imaging apparatus that is comprised of a Ti:Sapphire laser for generating a narrow beam of ultra-short optical pulses, a photo cathode for converting the optical pulses into short electron pulses and then accelerating and focusing the electrons into an anode, which acts as a target and produces ultrashort x-ray pulses. Six or more detectors, either streak camera type detectors or high speed photoconductors, are placed around the object to be imaged/radiated, and the time resolved signals from each is recorded. This time of arrival is correlated with the time of creation of the x-ray pulse. Finally, processor means are provided for converting these measured signals and their time of arrival into an image of a three dimensional object. The particular method for converting these values is an important aspect of the invention.

According to the second preferred embodiment of the invention, the imaging apparatus again comprises a high intensity laser, a photocathode electron gun, and linear accelerator section to produce a high energy short pulse electron beam. This electron beam is then incident on a target to produce ultrashort x-ray pulses. Again, six or more detectors are placed around the object to be irradiated, and the time resolved signal from each is recorded. Processor means are provided for constructing the three dimensional image and the corresponding x-ray radiation dose distribution.

The invention is further described by its preferred embodiments that should be considered in connection with the following drawings.

DETAILED DESCRIPTION OF A PREFERRED EMBODIMENT

Figure 1:
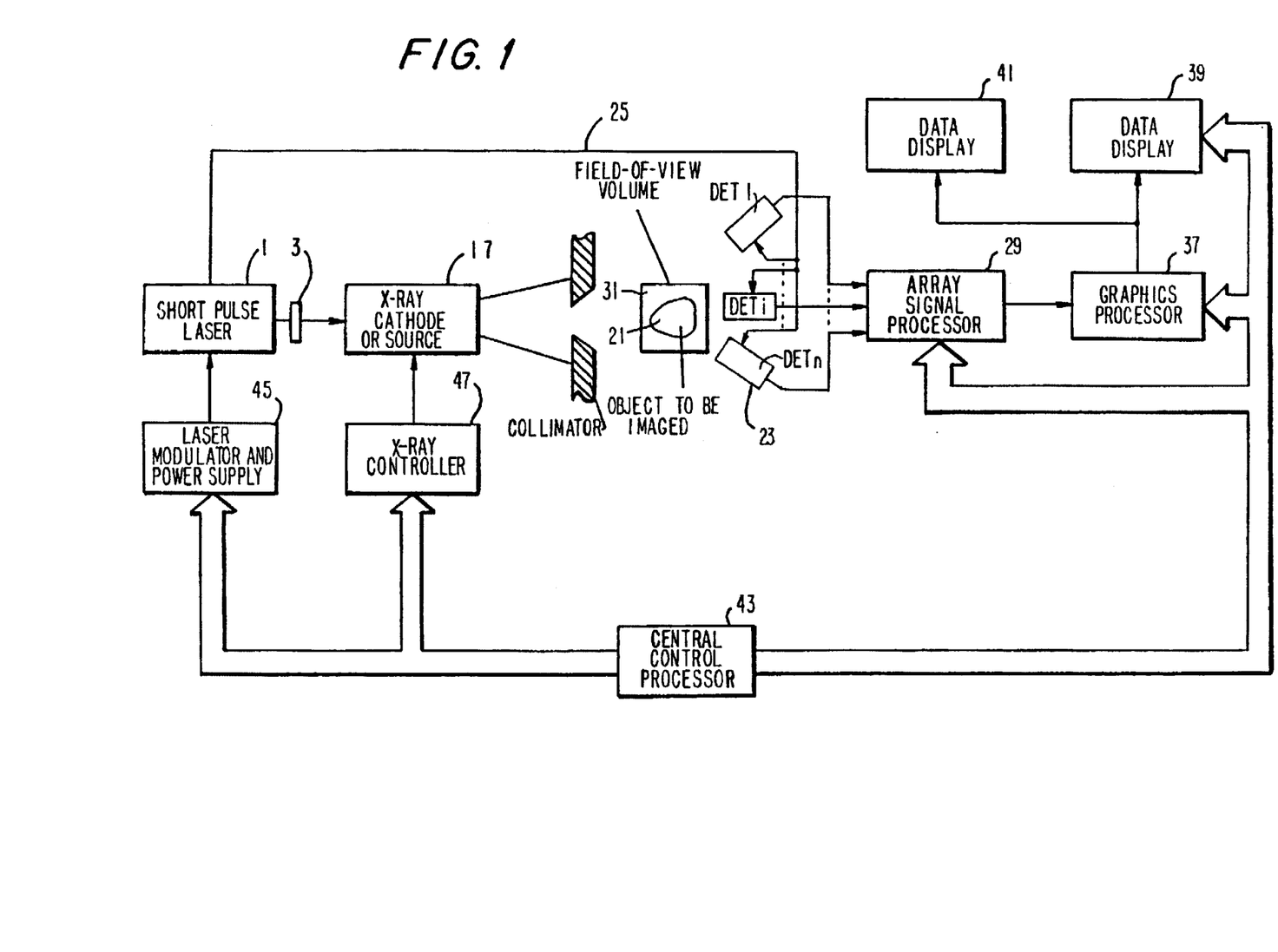
FIG. 1 is a block diagram illustrating the interconnection of the components of a preferred embodiment of the present invention.
Figure 2:
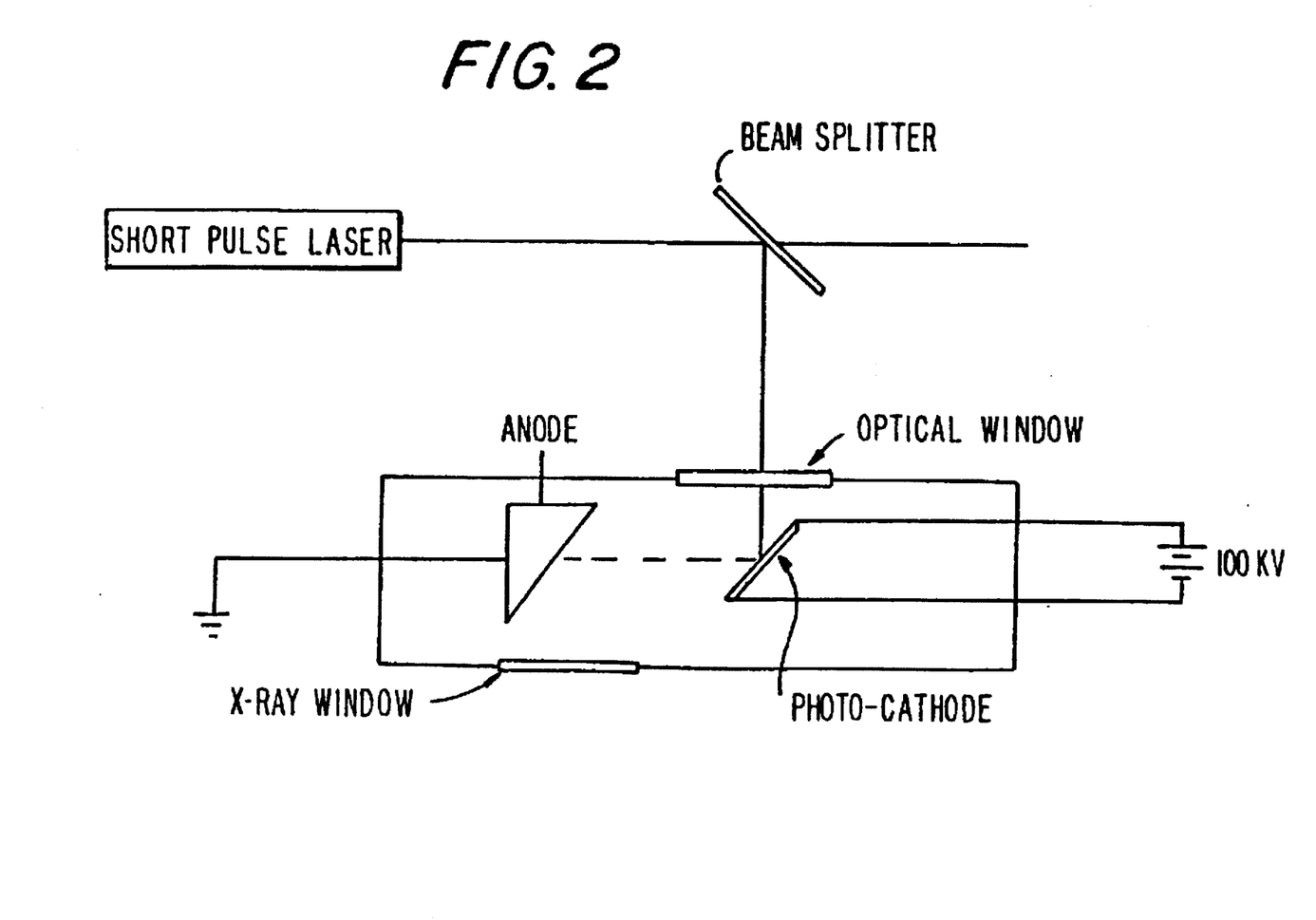
FIG. 2 is a schematic diagram of a high repetition rate ultrashort x-ray pulse generator.
Figure 3:
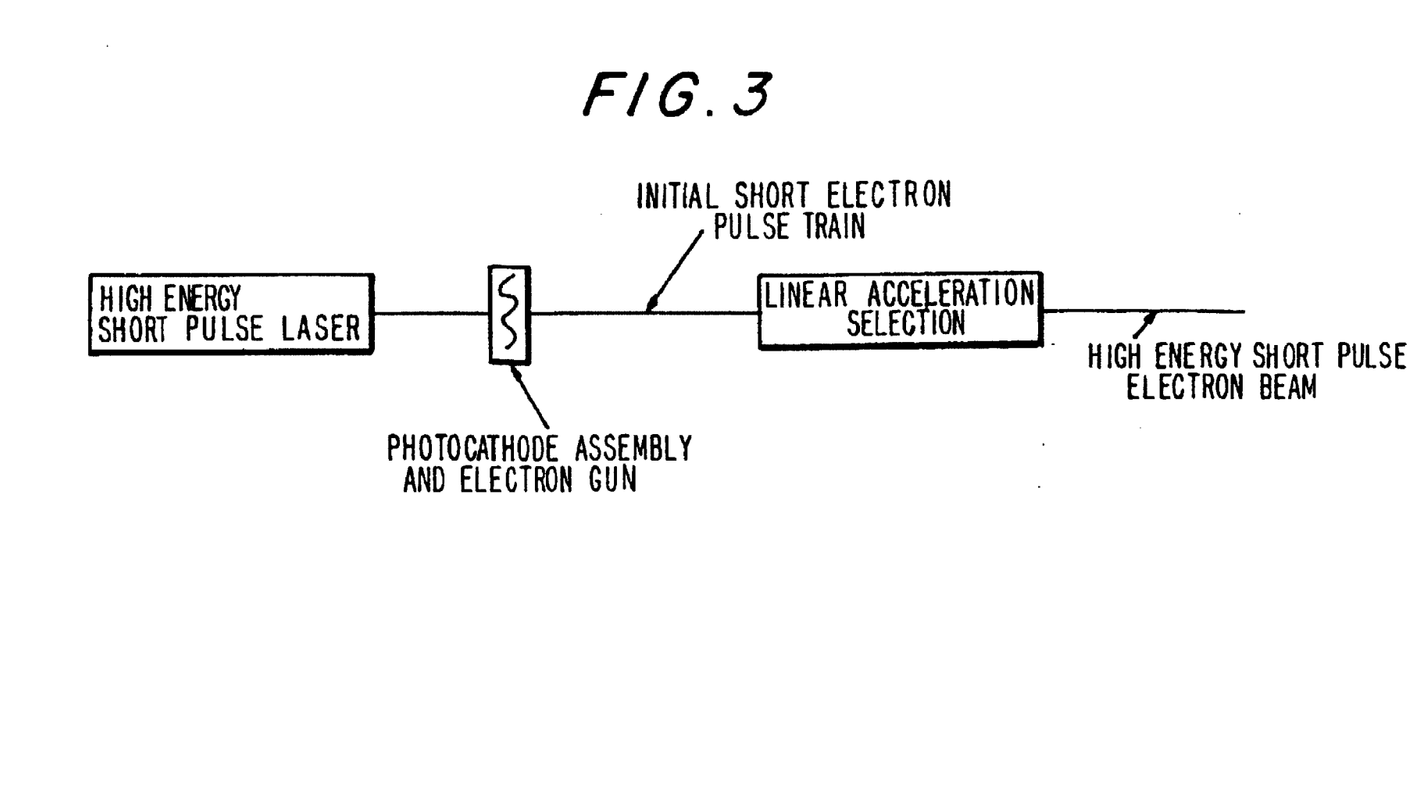
FIG. 3 shows a higher energy ultrashort x-ray pulse generator.

The block diagram in FIG. 1 shows an overview of the imaging system. A picosecond or subpicosecond pulsed laser such as a any sub-picosecond laser with average power of approximately 100 milliwatts such as a mode locked Ti:Sapp laser for lower energy/high repetition rate or a synchronously pumped dye laser system. For higher energy/low repetition rate a multi staged dye laser may be used or any laser capable of delivering at least one millijoule per pulse with pulse width less than about one picosecond. The laser radiation is incident on a photocathode apparatus 3 shown in greater detail in FIG. 2. The photocathode apparatus 3 comprises a beam splitter 5 to deflect a portion of a pulse from the laser 1 through an optical window 7 onto a photocathode 9 and accelerator section 11. The configuration shown is appropriate for relatively low energy x-ray generation, typically x-rays having an energy of about 100 keV. An alternative embodiment provides higher energy x-rays up to typically 50 meV by employing a higher energy source of photons and electrons for the production of more penetrating x-rays such as type of short pulse electron sources found in photocathode driven free electron lasers variety used at either Vanderbilt University or Brookhaven National Laboratories Free Electron Laser facilities and are shown in FIG. 3.

Returning to FIG. 2, there is shown an anode 13 within the accelerator section 11 arranged so that the electrons emitted from the photocathode 9 are accelerated onto the anode. The sudden deceleration of the electrons as they strike the anode 13 produces x-rays that can exit from the acceleration section 11 through the x-ray window 15.

The photocathode and anode together comprise the x-ray cathode or source 17 depicted in FIG. 1. The x-rays emitted from the source 17 pass through a collimator 19 to impinge on a field of view volume of the object 21 to be imaged and then on a plurality of x-ray detectors 23. The collimator 19 is a heavy metal alloy such as those used in radiation therapy machines. The collimator passes only x-rays in a particular direction.

Figure 4:
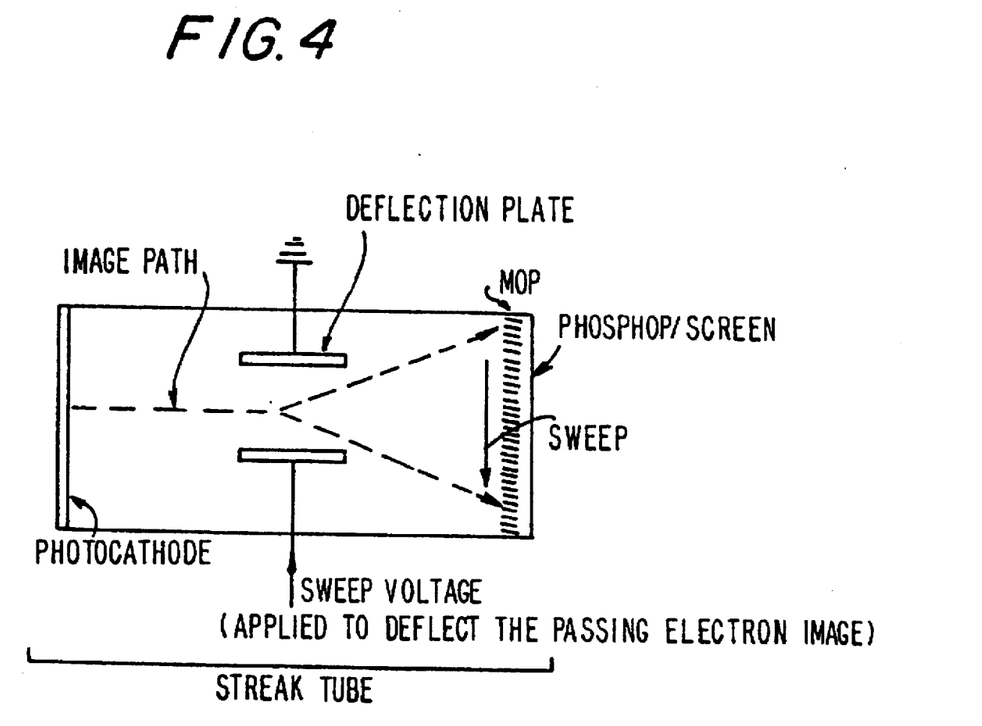
FIG. 4 shows a streak tube detector.
Figure 5:
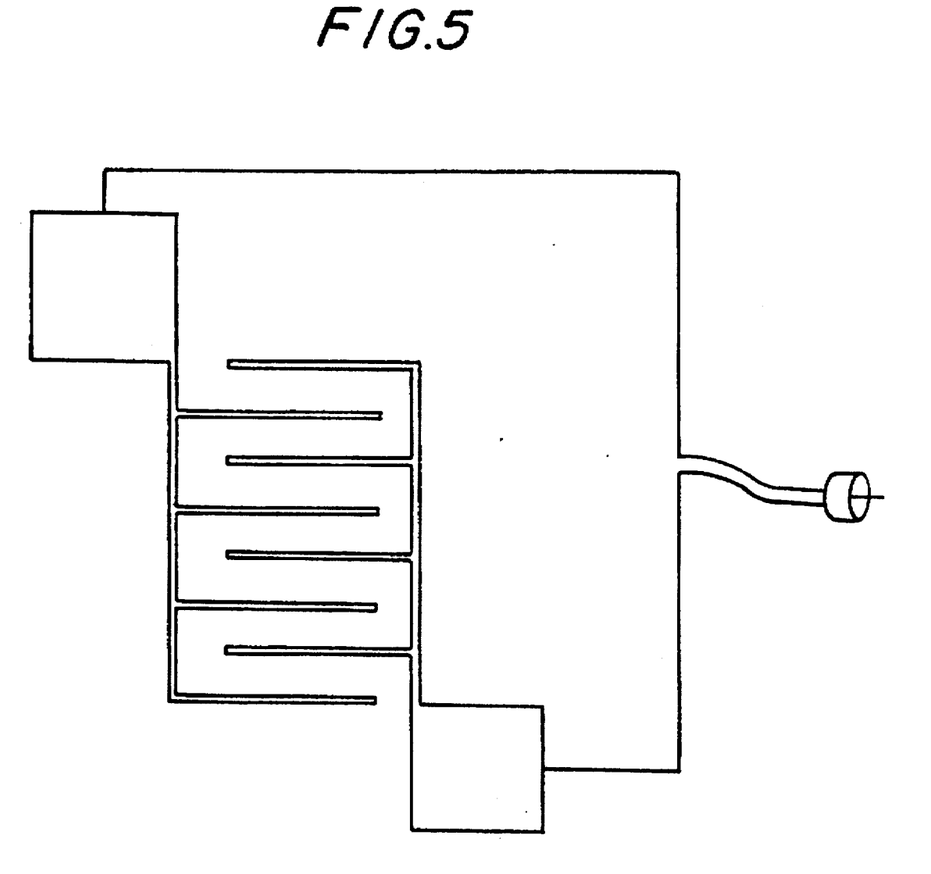
FIG. 5 shows an interdigitated detector.

The x-ray detectors 23 can either be streak camera detector's as shown in FIG. 4 and manufactured by Cordin Cameras, or may be interdigitated solid state detectors consisting of a metal pattern as shown in FIG. 5 deposited on a GaAs or other suitable high speed substrate. Typical dimensions between the digits would be <5 microns. Such devices are available for purchase either from Emory University laboratories or from Picometrix. In an inter-digital detector, metal "digits" are deposited on low temperature GaAs or other high speed substrates and biased through a low capacitance connector. A signal line 25 also connects the short pulse laser 1 to the detectors 23, to provide timing signals that enable correlation of the time of departure of the light pulse from the laser with the arrival of x-rays at the detectors. The detectors 23 provide signals along signal lines 27 to an array signal processor 29. These signals indicate both the intensity of detected x-ray radiation and the time of arrival of the x-rays as well as the time of emission of the laser pulse.

The detector array signal processor 29 is preferably a Unix type workstation such as a Sun SPARC station or a Hewlett Packard Unix Station. The workstation is equipped with conventional data acquisition circuit boards (not shown) such as those available from the workstation manufacturer or available as IBM PC compatible boards. In the latter case, the array processor will also include a small IBM PC or PC clone type circuit board dedicated to running the data acquisition hardware. The data display, data storage unit, and graphics processor are all part of the workstation. The central control processor will include a software program to be described below that will be executing on the workstation as well.

In operation, the short pulse laser 1 generates ultra short laser pulses (<1 picosecond, preferably from 40 femtoseconds) (40×10$^{-15}$ sec.) to 1 picosecond (10$^{-12}$ sec.) which are then incident on the photocathode 9. The photocathode then emits a short pulse of electrons which are accelerated into an anode or target 13. The target, in turn, radiates short x-ray pulses. Image resolution is directly related to the x-ray pulse width by the relationship: maximum resolution= (speed of light)×(pulse duration); for a 100 fsec pulse the maximum resolution is 30μ. For a 1 psec pulse it is 300μ. For 1 nsec pulse it is 30 cm.; the shorter the pulse width the better the image resolution. Typical x-ray pulse widths are 1–2 picoseconds.

The emitted x-ray short pulses are collimated by the heavy metal collimator 19. The opening of the collimator is either a circular or square hole which creates a conical x-ray pattern as opposed to an omnidirectional 4 pi steradian x-ray pattern. The collimator may be fashioned as heavy metal walls that absorb all x-ray energy except those that pass through its circular or square hole. The conically expanding x-ray pulse illuminates the field-of-view volume which contains the object 21 of interest that is to be 3-D imaged.

The x-ray photons of the very short x-ray pulses are scattered by the atoms of the target. In general, the level of scattering is a function of the x-ray cross-section of the target's individual atoms multiplied by the density of the target's atoms. In this case, since the scattering to be detected will be Compton scattering, the level of scattering will be a function of the target's electron density. If the target is a complex, heterogeneous material, such as organic material (an apple, a lung, etc.), the scattering will be very complex and therefore a methodology has been invented for detection and processing.

A number of detectors 23 are used to detect the scattered x-ray pulses. They are placed at various known angles and ranges relative to the field-of-view volume. In selecting these angles one may take advantage of the sin$^2$(θ/2) behavior of the Compton scattering pattern. The time that the scattered short pulse x-rays are detected at each detector is used to determine the total path length from the x-ray source to the detector.

Figure 7:
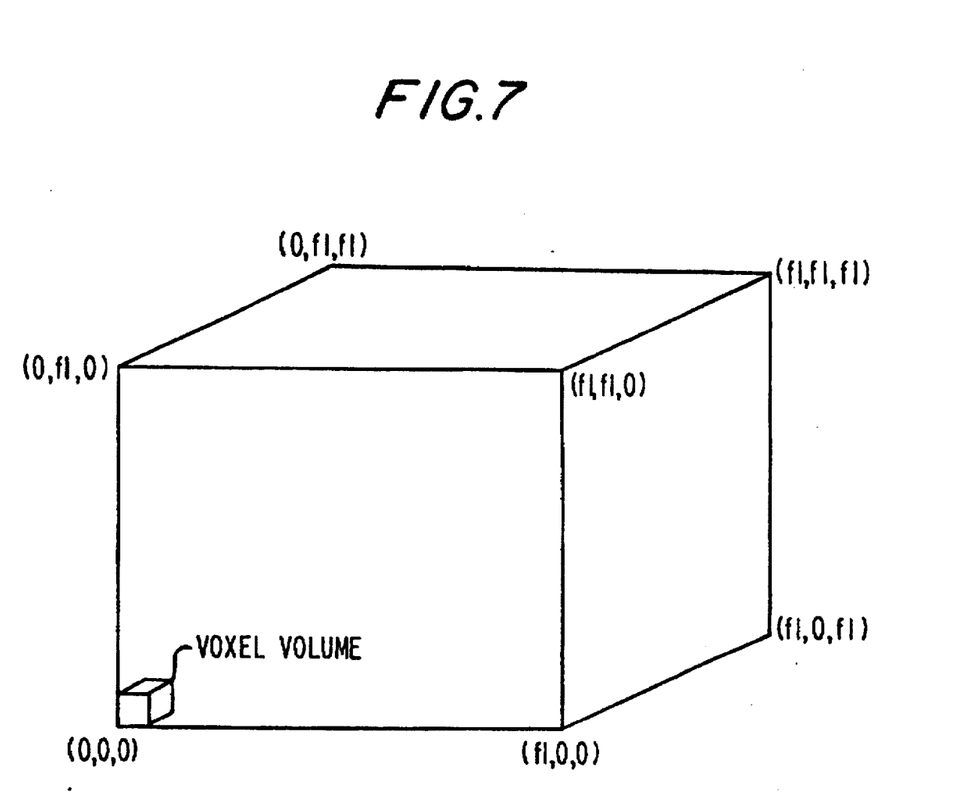
FIG. 7 is a diagram showing the geometric arrangement of a field of view volume for the measurement scheme.

Since the position of each detector is known to within a tolerance, and the time evolution of the received signal is known within a tolerance, the information from an array of detectors is used to create a three dimensional image of the target or any portion of the target. This is done in the array signal processor 29. As shown in FIG. 7, the field-of-view volume 31 may be considered to be a three dimensional cube where each side 33 is defined as the field length, fl. The cube is divided into small cubic volumes 35 where each side of these small cubes has a length, $I_V$, equal to the product of the speed of light and the pulse width of the short x-ray pulses. For a pulse width of one picosecond, 1×10$^{-12}$ seconds, and a speed of light of 3×10$^8$ meters/sec, the side length of the small cube, $I_V$, is 3×10$^{-4}$ meters or 0.3 millimeters. The total number of these small cubes in the field-of-view volume is (fl/$I_V$)$^3$. Each of these small cubes defines the physical boundaries of a voxel that is used to generate a 3-D image.

The array signal processor 29, using a unique processing algorithm to be described below, calculates the amplitude of the scattered x-ray pulses in each of the small cubes, and assigns this amplitude to a memory location within the processor 39 for each of the small voxels in a linear array of data. The linear array of voxel data is handed off to a standard graphics processor 37 which employs standard 3-D graphics software (e.g. the standard x-windows 3D graphics package) for creating the desired image data. This data may be visually presented by a data display unit 41 such as a computer monitor and/or stored by a data storage unit 39 such as a read write optical disk or tape for further analysis.

A use for the data display capabilities of the invention is to provide a three dimensional image (by using standard software to provide sections or surface renderings) of radiation dosages during x-ray therapy.

A central control processor 43 is used to control a laser modulator to maintain the laser in its short pulse mode and power supply unit 45, an x-ray controller 47 to allow on/off control of the x-ray source and current control, the array signal processor 29, the graphics processor unit 37, and the data storage unit 39. The central control processor comprises a ROM or RAM having a program that runs on the workstation that allows the user, perhaps an x-ray technician, to run the system. A general user interface or GUI (not shown) connects the user to the hardware.

Figure 6:
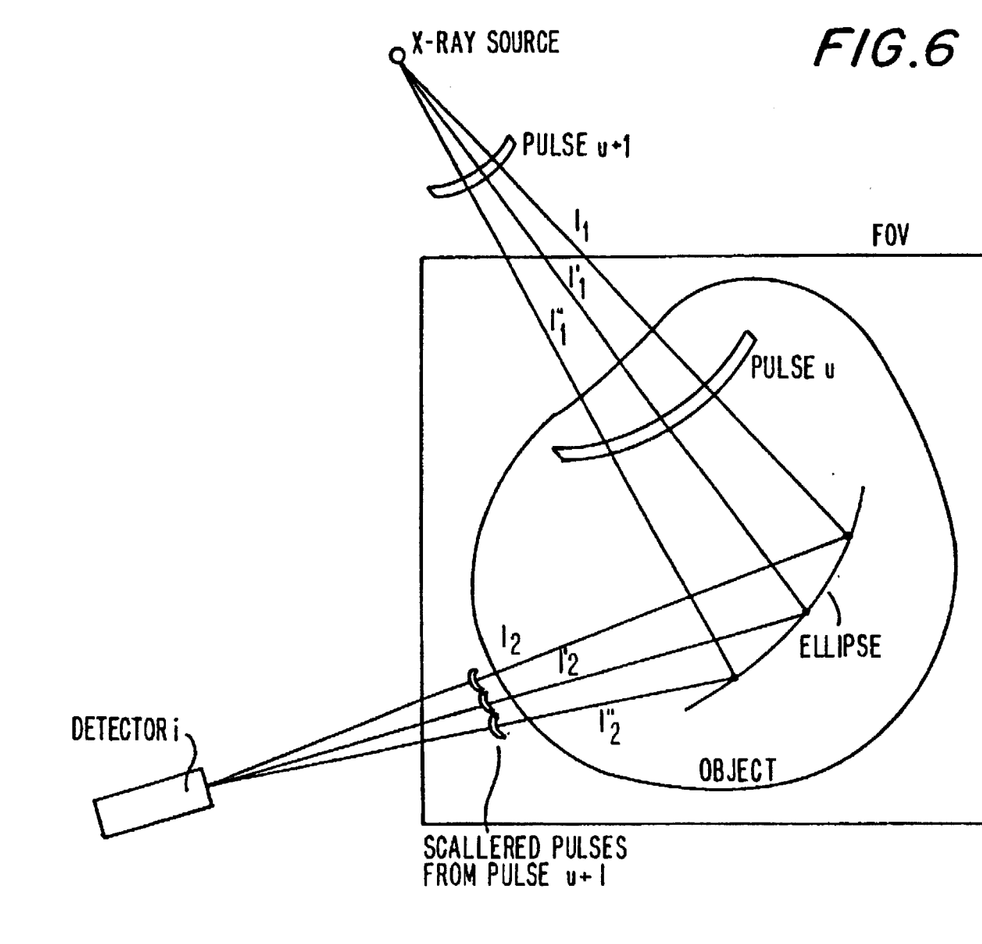
FIG. 6 is a diagram showing the time evolution of a single pulse radiating from an ultrashort x-ray source through an object to a detector.
Figure 12:
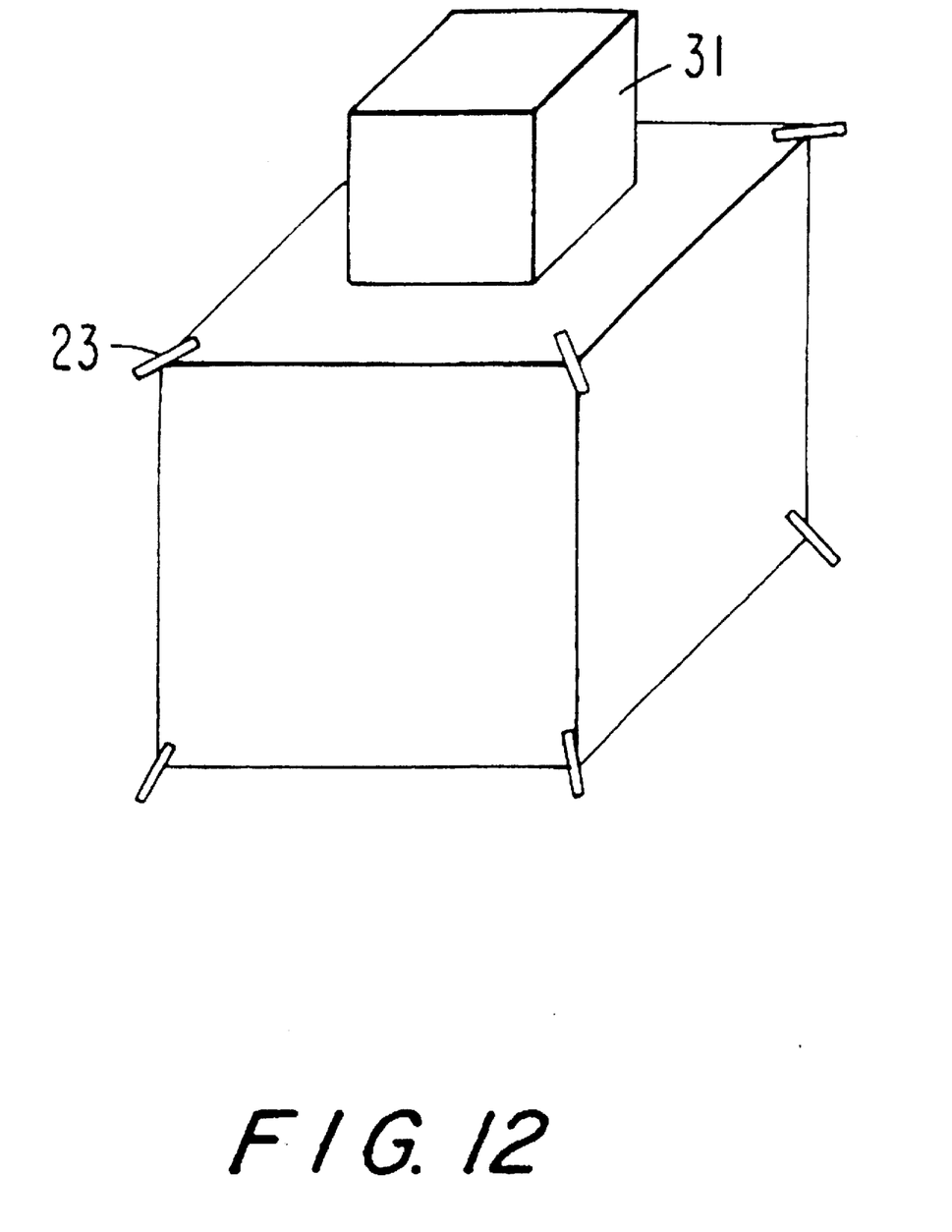
FIG. 12 is a 3-depiction of the arrangement of the detectors and the field of view volume as shown schematically in FIG. 1.

FIGS. 6, 7 and 12 illustrate geometrically the measurement scheme. In FIG. 6, a point P lies inside the field of view 31 and is a distance $I_1$ from the x-ray source and a distance $I_2$ from the i'th detector 49, which is one of the detectors 23 shown in FIG. 1. It takes a photon t=($I_1$+$I_2$)/c seconds to go from the source to point P and then to be scattered to the i'th detector. There are many voxels P' that have associated path lengths $I_1$' and $I_2$' such that $I_1$+$I_2$=$I_1$'+$I_2$'. All of these voxels will make up an ellipsoidal surface of revolution called the shell of the i'th detector at time t and is denoted shell$_i$(t). As shown, this is a set of points and not a single point.

As shown in FIG. 12, the detectors 23 may be arranged in a regular pattern located at the corners of a cube. Other regular polyhedra may be substituted for the cube.

Figure 8:
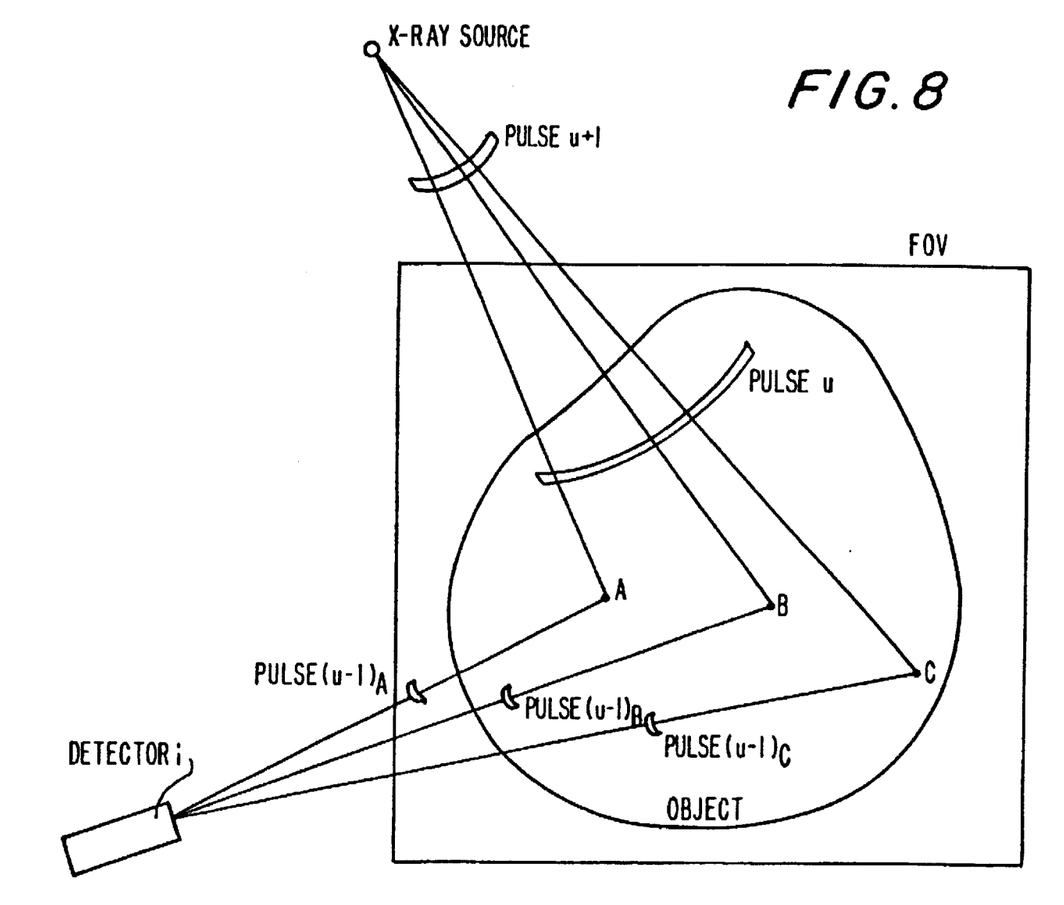
FIG. 8 is a diagram showing the scattering of pulsed x-rays from a single point source from three separate locations in the object to be imaged.

In FIG. 8, scattering of a single pulse, (u–1), from three arbitrary points in the FOV is illustrated. Since these points are not assumed to lie on a single ellipsoidal surface t these pulses a,b,c, as received by detector i, are not time coincident.

The attainable resolution of the system is determined by the x-ray pulse duration $t_{pulse}$, the active area of the detectors, and the rise time of the detectors. The upper limit of this resolution, denoted res$_{max}$, is equal to the relation c/$t_{pulse}$ where c is the speed of light. The impulse response function of the detectors (assuming they are all identical) is called h(t). If the time evolution of a single pulse is denoted x(t) then the output y(t) from a detector measuring a single x-ray pulse directly will be given by the relation:

$$y(t)=\int x(\tau)h(t-\tau)d\tau$$

In theory the impulse response of the detector could be measured and the actual signal x(t) could be recovered from y(t). This procedure is difficult to implement unless the signal to noise ratio is on the order of 100. Consequently, we call the resolution of our detector the full width at half maximum, or FWHM, of the response function h(t). If this is less than or equal to $t_{pulse}$ then the resolution of the system will be res$_{max}$, otherwise the resolution of the system will be given by the relation c/FWHM. Furthermore, the size of the detector will affect the resolution of the system.

In the previous description of the elliptical shells of a given detector, the detector was implicitly assumed to be a point. If the detector has a finite size, then any two points on the detector will have slightly different elliptical shells. The maximum distance between these shells will be the largest dimension of the detector times the sine of the angle of the maximum acceptance of the detector. Typically this will be smaller than c/FWHM. If it isn't, however, then this distance is the resolution of the system. In the following discussion, the resolution of the time signal is defined as the spatial resolution of the system divided by the speed of light.

Three dimensional image reconstruction involves manipulation of spatial and time data from all n detectors of the system. This is accomplished by the processing algorithm. The voxel space will be called the field of view or FOV. The maximum time we need to consider will be determined by the size of FOV and will be called $t_{max}$. The quantity dt represents the time resolution of our measurement system and determines the voxel volume. The i'th detector's measured signal at time t will be $sig_i[t]$.

Figure 9:
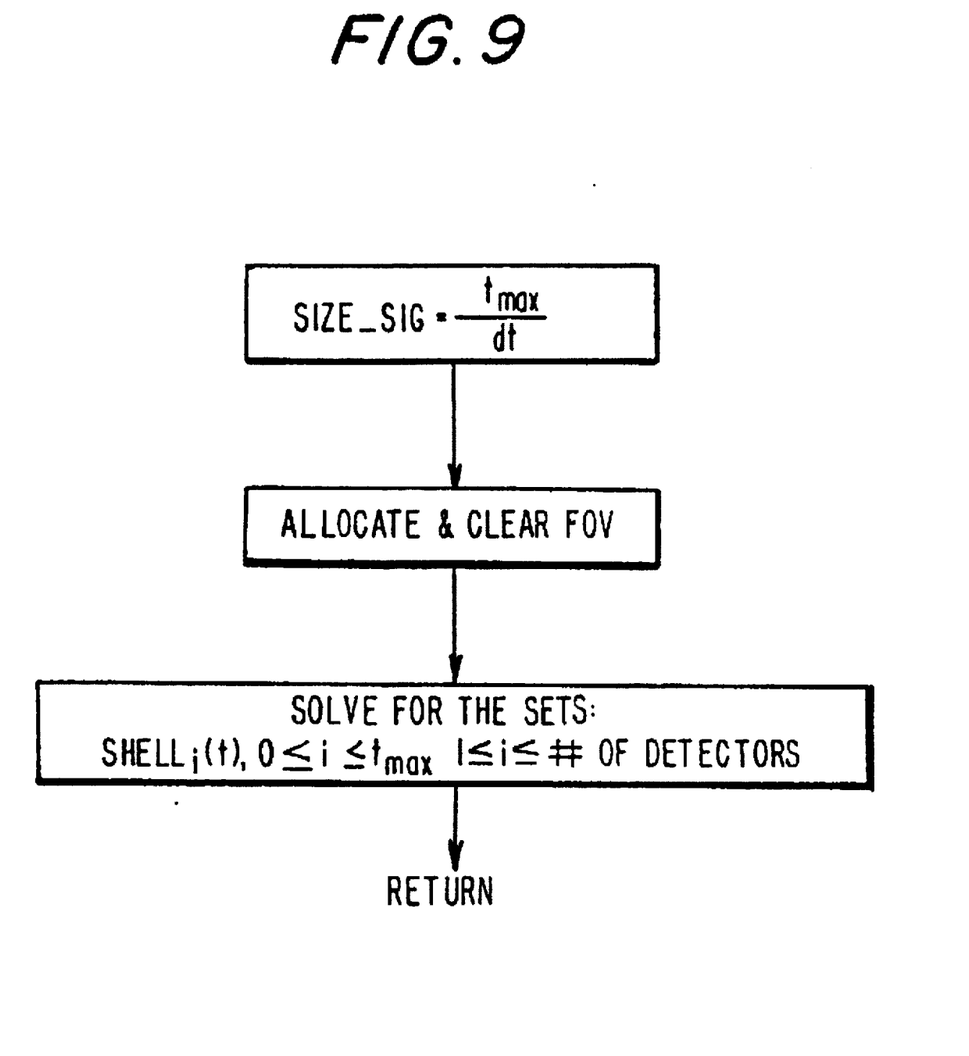
FIG. 9 is a flow chart of an overview of the reconstruction algorithm employed in the processor of the present invention.
Figure 10:
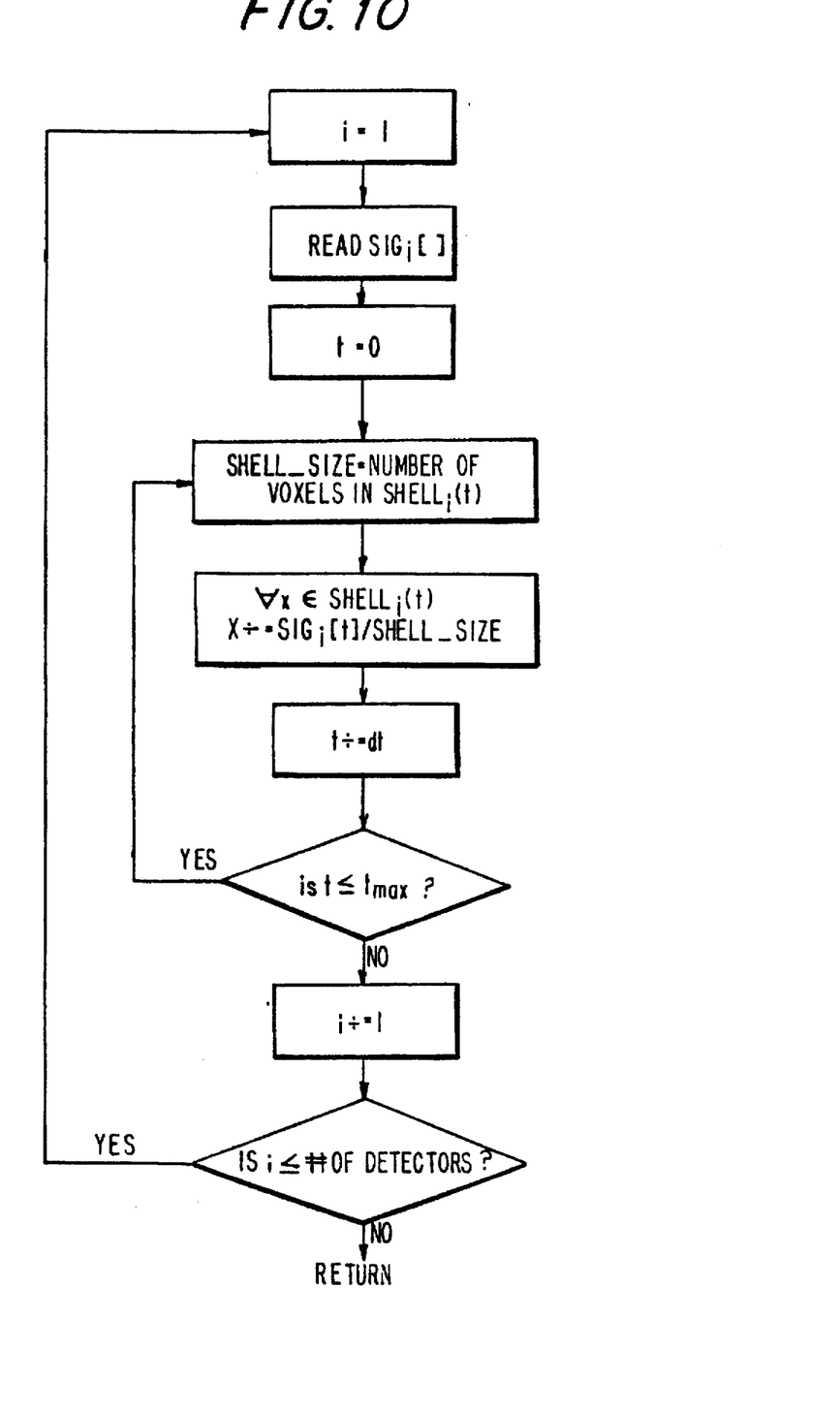
FIG. 10 is a flow chart of the first construction of the reconstruction algorithm of the present invention.
Figure 11:
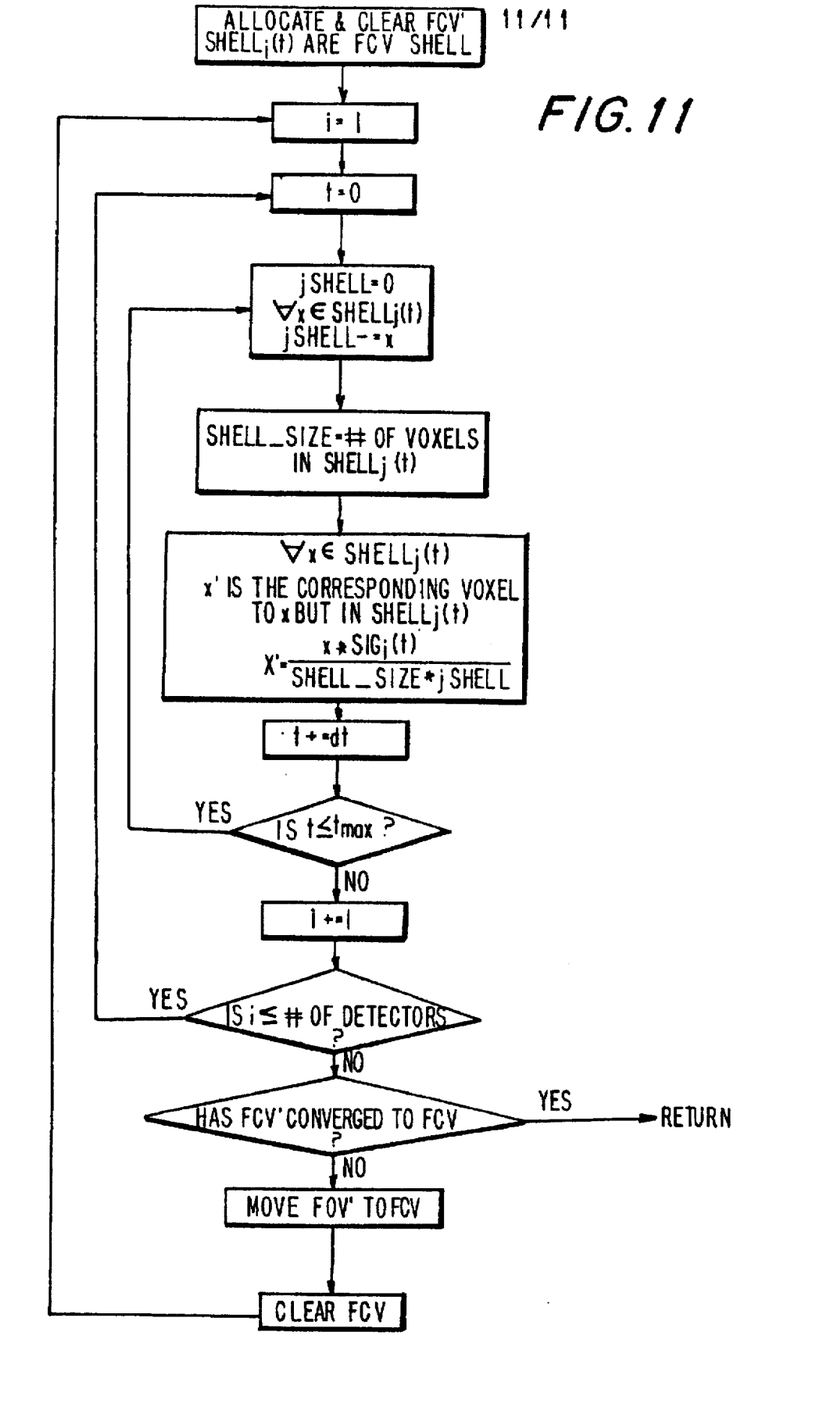
FIG. 11 is a flow chart of the second construction of the reconstruction algorithm of the present invention to refine the resulting image.

The steps for converting the measured signals into a three dimensional image are termed the initial setup, the first construction, and the image refinement. The flow charts depicted in FIGS. 9, 10, and 11 show these steps in detail. When the procedure is finished the information in the FOV array is displayed using standard three dimensional graphics software.

Image data is stored in a linear array. The size of the array is determined by the field-of-view volume and the obtainable resolution. If the image array is called FOV[ ] then the label or address of each voxel in the image is defined by its (x,y,z) coordinates using the relation:

$$voxel(x,y,z)=FOV[z*fl^2+y*fl+x]$$

where fl is the field length and x,y,z range from 0 to fl−1. The size of FOV is given by the relation $$sizeof(FOV)=(fl/resolution)^3$$

If the field length is 10 centimeters and the desired resolution is 0.1 centimeters (1 mm) then the size of FOV must be 1,000,000. If the desired field of view is not a cube then the size of FOV will by analogy be the volume of the field of view in the unit system where the resolution has dimension 1.

As shown in FIG. 9, the image reconstruction begins by determining the number of time intervals size_sig to be measured, and setting all the voxels to zero. The time evolving signal from the first detector is sampled every dt. The ellipsoidal surface corresponding to each dt is determined, and to each voxel in FOV[ ] that lies on that ellipsoidal surface is added a number equal to the value measured at the detector divided by the number of voxels that the ellipsoidal surface contains. This procedure is then repeated for each of the detectors. This process is essentially a re-normalization of the data, which is repeated until consistency is achieved. The flow chart for this procedure is shown in FIG. 10. This will yield the first construction of the image. This is an approximation to the image that becomes exact if there are an infinite number of detectors uniformly distributed in space.

Next the image goes through an iterative procedure that repeats until the image is self consistent. As shown in the flow chart of FIG. 11, a second three dimensional voxel space FOV'[ ] is set up and cleared. The values of the voxels from the first image that lie on the "first" ellipsoid of the first detector are summed together and divided by the number of voxels on that surface. This yields the integrated weight. Then into each voxel in the FOV'[ ] corresponding to the "first" ellipsoid of the first detector is added the corresponding value from FOV[ ] multiplied by the first sampled value from the detector and divided by the integrated weight. This is repeated for all ellipsoids and all detectors. The process is then repeated, going this time from FOV'[ ] to FOV[ ]. The iterations continue back and forth until the image in FOV and FOV' are the same. This self consistent image is the refined image that can then be displayed using standard three dimensional techniques.

A specific implementation of an algorithm for construction of the image is given in C-language source code in Table A. This may be compiled on any standard compiler. Stdio.h and math.h are conventional input/output and mathematics libraries. This algorithm is capable of handling $10^6$ data points/sec on a PC, with correspondingly greater speed on a mainframe.

While there have been shown and described and pointed out the fundamental novel features of the invention as applied to preferred embodiments thereof, it will be understood that various omissions and substitutions and changes in the form and details of the device illustrated and in its operation may be made by those skilled in the art without departing from the spirit of the invention. It is the intention, therefore, to be limited only as indicated by the scope of the claims appended hereto.

What is claimed is:

1. An apparatus for imaging the interior of an object located in a field of view volume comprising a source of a ultra short collimated x-ray pulse emitted at a first time having a predetermined energy spectrum and direction passing through said field of view volume, a detector array comprising a plurality of x-ray detectors each having timing and detection means to enable detection at a second time of the intensity of x-ray pulses Compton scattered by said object, wherein said second time follows said first time, array signal processor means for receiving from said source of said x-ray pulse a signal indicative of said first time and for receiving from said detector array signals indicative of said second time and said intensity signal from said detector array and for transmitting image data indicative of the location and density of the scattering center producing the scattered radiation, graphics processor means for receiving said image data from said array signal processor, wherein said image data may be stored and/or displayed on data display or data storage means.

2. The apparatus of claim 1, wherein said array signal processor comprises data storage means and means to determine a time interval between said first and said second time and to store in said data storage means data corresponding to voxel locations in said field of view volume, wherein said data is incremented for each voxel element lying on an ellipsoidal surface in said field of view volume, said ellipsoidal surface having a semi-major axis length equal to half the said time interval multiplied by the speed of light and focal points at said source and said x-ray detector.

3. The apparatus of claim 2, wherein said array signal processor further comprises means to accumulate data in said data array corresponding to each x-ray detector in said detector array until self consistent values are obtained.

4. The apparatus of claim 2 wherein said data increment is equal to the intensity signal from said detector array divided by the number of voxels on said ellipsoidal surface.

5. The apparatus of claim 1 wherein said source of ultra short x-rays comprises an optical laser adapted to provide intense pulses to a photocathode to produce electrons, electron accelerator means to increase the energy of said electrons and to direct them onto a target to produce x-rays by deceleration, collimator means to allow a narrow conical bundle of said x-rays to impinge on said object in said field of view volume.

6. The apparatus of claim 1 wherein said source of ultra short collimated x-rays comprises apparatus for therapeutic x-ray treatment of a patient and said data display is a three dimensional display of dosage received by the patient.

7. The apparatus of claim 1 wherein said detector array comprises individual detectors at the corners of a regular polyhedron.

8. The apparatus of claim 7 wherein said regular polyhedron is a cube.

* * * * *